(12) United States Patent
Desai et al.

(10) Patent No.: US 6,972,083 B2
(45) Date of Patent: Dec. 6, 2005

(54) ELECTROCHEMICAL METHOD AND SYSTEM FOR MONITORING HYDROGEN PEROXIDE CONCENTRATION IN SLURRIES

(75) Inventors: Vimalkur Haribhai Desai, Orlando, FL (US); Dnyanesh Chandrakant Tamboli, Orlando, FL (US)

(73) Assignee: Agere Systems, Inc., Allentown, PA (US)

( * ) Notice: Subject to any disclaimer, the term of this patent is extended or adjusted under 35 U.S.C. 154(b) by 468 days.

(21) Appl. No.: 10/259,254

(22) Filed: Sep. 27, 2002

(65) Prior Publication Data

US 2004/0069625 A1    Apr. 15, 2004

(51) Int. Cl.[7] ......................................... G01N 27/416
(52) U.S. Cl. ..................... 205/782; 205/786; 204/400; 204/412
(58) Field of Search ............... 204/400, 409, 204/411, 412, 434; 205/782, 786, 775; 451/41

(56) References Cited

U.S. PATENT DOCUMENTS

| | | | |
|---|---|---|---|
| 4,072,594 A | * | 2/1978 | Outsuka et al. ............. 204/406 |
| 4,384,925 A | * | 5/1983 | Stetter et al. ............ 205/785.5 |
| 5,637,031 A | | 6/1997 | Chen |
| 5,686,829 A | * | 11/1997 | Girault ......................... 324/72 |
| 5,846,398 A | | 12/1998 | Carpio |
| 5,948,236 A | * | 9/1999 | Lipsztajn ................. 205/778.5 |

OTHER PUBLICATIONS

Cosgrove et al, Analyst, 1989, vol. 114, pp. 1627-1632.*
Skoog, Principles of Instrumental Analysis, 1985, pp. 627-630.*
Bard and Faulkner, Electrochemical Methods, 2nd Edition, 2001, pp. 24-28.*

* cited by examiner

Primary Examiner—Kaj K. Olsen

(57) ABSTRACT

Electrochemical monitoring system and method are provided for online determination of hydrogen peroxide concentration in slurries, e.g., a chemical mechanical polishing slurry. The monitoring system includes an electrochemical cell fluidly coupled to receive a slurry including hydrogen peroxide. The cell includes at least a working electrode made up of tungsten, a reference electrode and a counter electrode. The system further includes a potentiostat electrically coupled to the working electrode to supply a desired potentials in increments to the working electrode and measure current flow between the working electrode and the counter electrode. The amount of passive current established between the working electrode and the counter electrode over a selected time window is indicative of the concentration of hydrogen peroxide in the slurry.

6 Claims, 4 Drawing Sheets

ELECTROCHEMICAL METHOD AND SYSTEM FOR MONITORING HYDROGEN PEROXIDE CONCENTRATION IN SLURRIES

BACKGROUND OF THE INVENTION

The present invention is generally related to electrochemical techniques, and, more particularly, the present invention is related to electrochemical method and system for monitoring hydrogen peroxide concentration in slurries.

In the field of integrated circuit fabrication, it is known to polish a semiconductor wafer to achieve a planar surface on one or both sides of the wafer. One method used to polish such wafers is chemical mechanical polishing (CMP), where a surface of the wafer is rubbed against a polishing pad in the presence of a slurry. Chemical slurry containing abrasive particles in conjunction with the polishing pad increases the material removal rate, and such a process is commonly referred to as chemical mechanical polishing (CMP).

In the event of CMP of tungsten or copper material, it is known that the removal rates with slurries including hydrogen peroxide are highly dependent on the oxidizer concentration. Unfortunately, hydrogen peroxide, when added to the slurry, tends to dissociate with time leading to altered polishing rates. One known procedure to monitor the hydrogen peroxide concentration generally involves cumbersome actions, such as:

(1) Removal of slurry samples from a distribution loop;

(2) Setting up and operation of a titration system, which may involve handling and replenishment of chemically aggressive agents; and (3) Measurements of the titration end-point and calculation of the concentrations of the hydrogen peroxide, generally requiring the involvement of a skilled operator.

The foregoing procedure is not easily adaptable for generally continuous online monitoring and is relatively time consuming and incrementally adds to the costs of the CMP process. In view of the discussion above, it would be desirable to provide more cost-effective techniques and tools for accurately monitoring the hydrogen peroxide concentration in slurries used for the removal of materials in a CMP process. It is further desired to use electrochemical polarization techniques for providing more user-friendly tools and techniques to accurately and inexpensively monitor hydrogen peroxide concentration in the slurry.

BRIEF SUMMARY OF THE INVENTION

Generally, the present invention fulfills the foregoing needs by providing in one aspect thereof, an electrochemical monitoring system including an electrochemical cell fluidly coupled to receive a slurry including hydrogen peroxide. The cell includes at least a working electrode made up of tungsten, and a counter electrode. The system further includes a potentiostat electrically coupled to the working electrode to supply a desired anodic potential to the working electrode and measure current flow between the working electrode and the counter electrode. The amount of passive current density measured by the above technique after a selected time window is indicative of the concentration of hydrogen peroxide in the slurry. The term "passive current density" is the steady state current established on the tungsten surface per unit area when anodic potential above a certain value is applied (e.g. 0.5 v with respect to a commercially available Ag/Agel reference electrode). Passive current is current measured at such steady state.

The present invention further fulfills the foregoing needs by providing in another aspect thereof, an electrochemically-based monitoring method that allows fluidly coupling an electrochemical cell to receive a chemical mechanical polishing slurry including hydrogen peroxide. The cell includes at least a working electrode preferably comprising tungsten, and a counter electrode. The method further allows applying a desired potential to the working electrode, and measuring current flow between the working electrode and the counter electrode, with the amount of passive current therebetween over a selected time window being indicative of the concentration of hydrogen peroxide in the slurry.

BRIEF DESCRIPTION OF THE DRAWINGS

The features and advantages of the present invention will become apparent from the following detailed description of the invention when read with the accompanying drawings in which.

DETAILED DESCRIPTION OF THE INVENTION

Overview

The inventors of the present invention have innovatively recognized that electrochemical polarization techniques may be employed for accurately and inexpensively monitoring hydrogen peroxide concentration in slurries for chemical mechanical polishing of tungsten or other materials. When tungsten is exposed to hydrogen peroxide, it forms an oxide, $WO_3$. The thickness of this oxide is determined by the hydrogen peroxide concentration and the passive current density is a measure of thickness and hence is related to the hydrogen peroxide concentration. The oxide thickness is inversely proportional to the peroxide concentration. For example, during the oxidation of tungsten in a hydrogen peroxide solution, passive current densities may be determined by the chemical dissolution rates of tungsten oxides at the oxide/solution interface since passive current density is inversely proportional to the oxide thickness. If the dissolution rate is sufficiently high, the steady state oxide film thickness at a given potential is reduced, and this would result in an increase in the passive state current density. Conversely, if the dissolution rate is sufficiently low, the steady state oxide film thickness at that potential is increased, and this would result in a decrease in the passive state current density.

More specifically, the dissolution of tungstic oxide ($WO_3$), for example, is linearly dependent on the hydrogen peroxide concentration, which is suggested by the linear relationship between the passive current density of tungsten and the peroxide concentration. The passive current density is generally independent for voltages above about 0.5 V with respect to a reference electrode. In one exemplary embodiment, a voltage potential of about 1.5 V was supplied at the tungsten/solution interface by a potentiostat connected between working electrode and a counter electrode. The passive current is monitored over a suitable time window until stable. Alternatively, one can wait a sufficient time to allow the process to stabilize or equilibrium to be established before making a current measurement. A typical wait time could be from about 300 seconds to about 900 seconds. It will be appreciated that the present invention is not limited to any specific duration for the time window.

Figure 1:
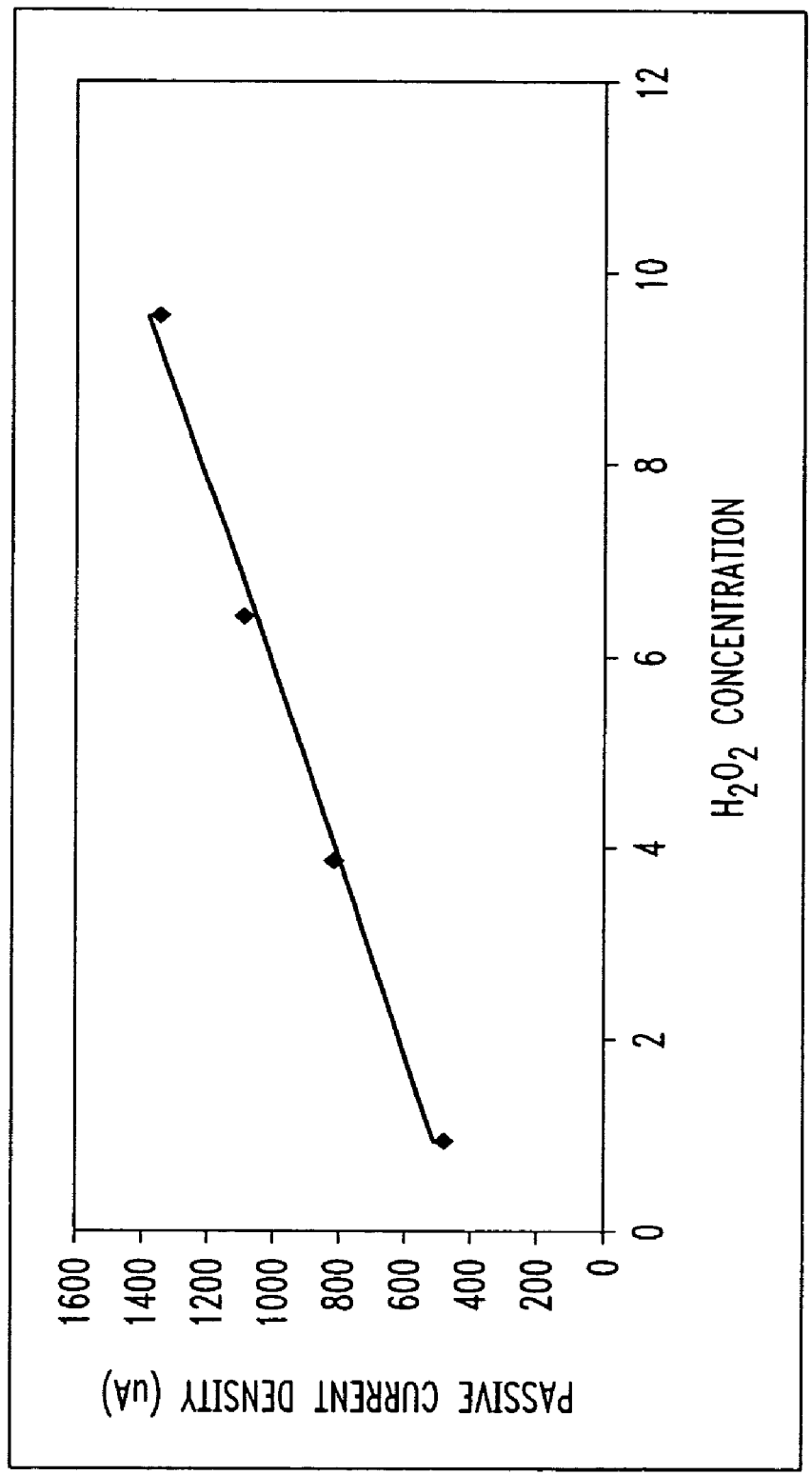
FIGS. 1–3 respectively show exemplary plots of passive current densities for tungsten as a function of hydrogen peroxide concentrations in a respective slurry under various conditions.
Figure 2:
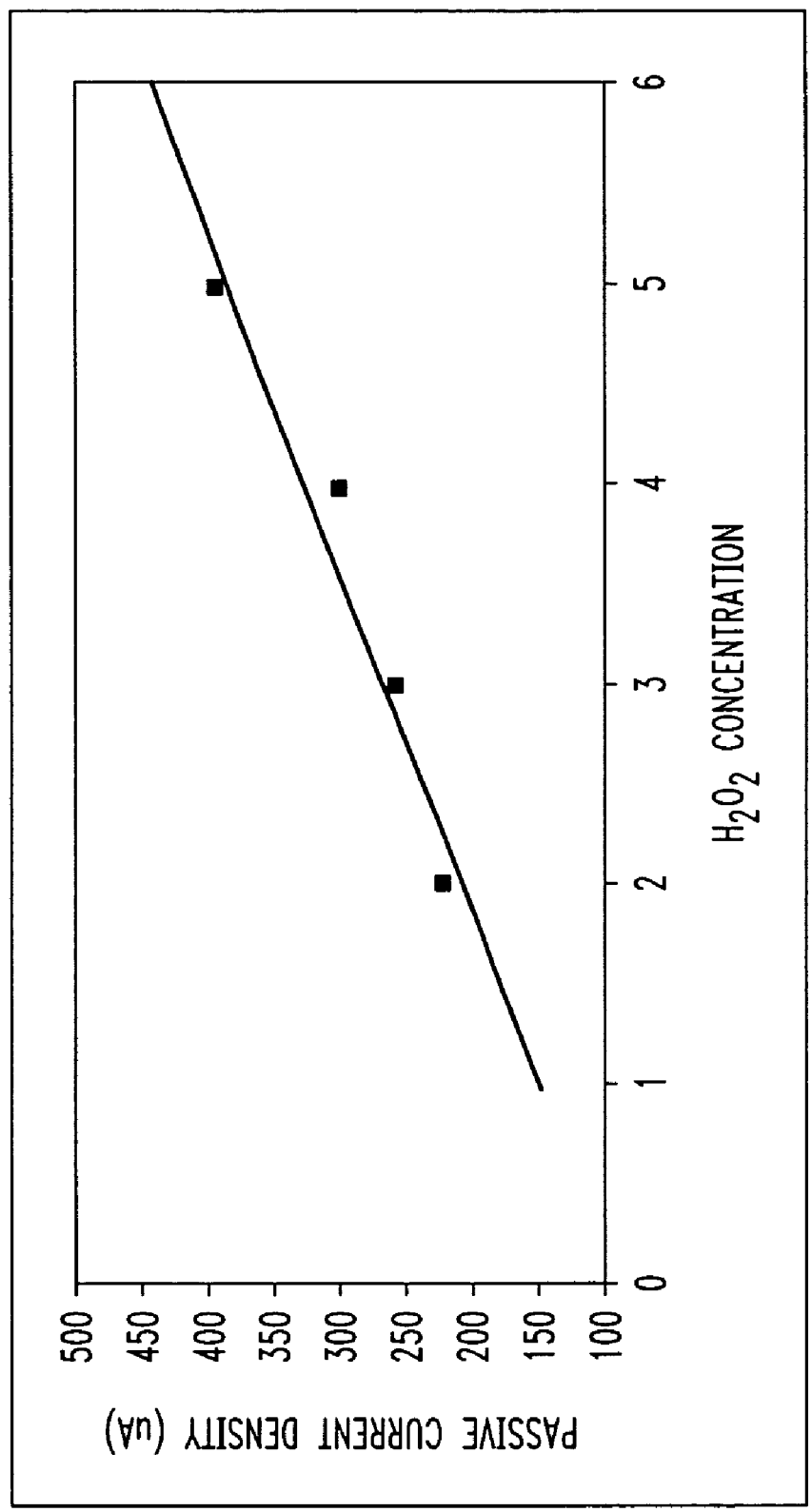
Figure 3:
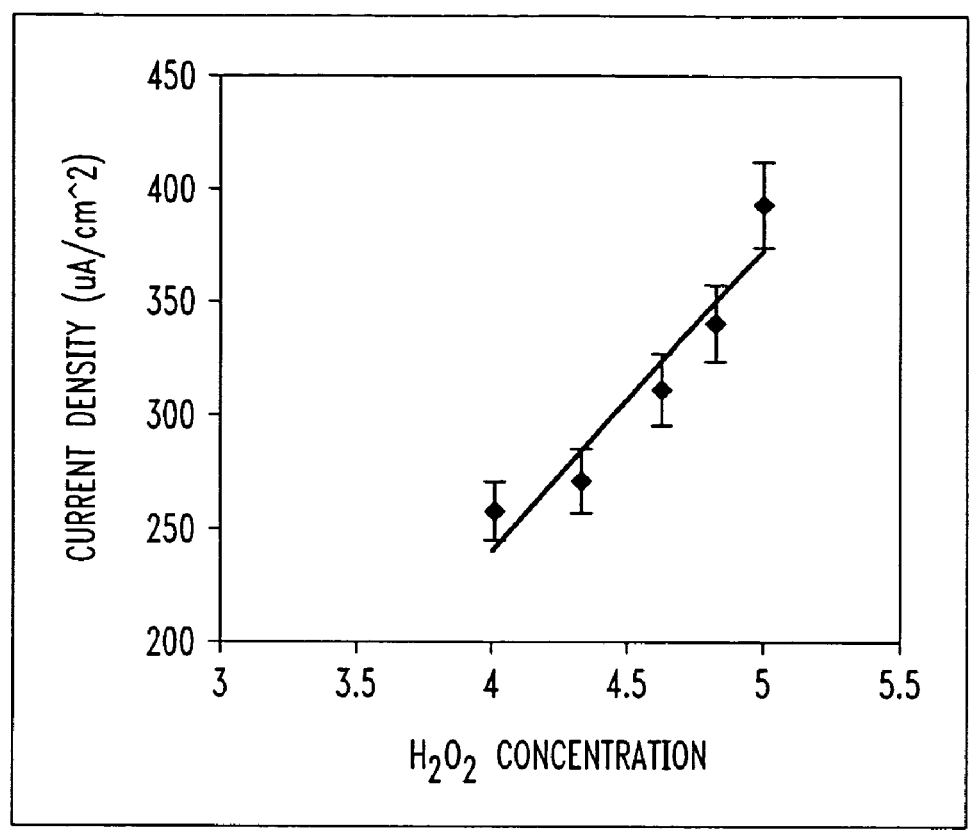

Experimental Results:

FIG. 1 shows an exemplary plot of passive current densities for tungsten as a function of hydrogen peroxide concentrations in a solution having a pH value of about four and using 0.1M of potassium nitrate ($KNO_3$) as a supporting electrolyte. It should be appreciated from the plot that the linear relationship extends over a relatively wide range of hydrogen peroxide concentrations. FIG. 2 shows another exemplary plot of passive state current densities of tungsten as a function of hydrogen peroxide concentrations in semi-sperse slurry. FIG. 3 shows still another exemplary plot of passive state current densities of tungsten as a function of hydrogen peroxide concentrations in semi-sperse slurry, in which an initial five percent weight concentration of hydrogen peroxide was successively altered by the addition of deionised water. Titrations with $KMnO_4$ were performed to independently measure the hydrogen peroxide concentration. As suggested above, linearity of the data is evident in each of these cases. As will be readily appreciated by those skilled in the art, sensitivity can be further enhanced by addition of suitable supporting electrolytes to the slurry.

Figure 4:
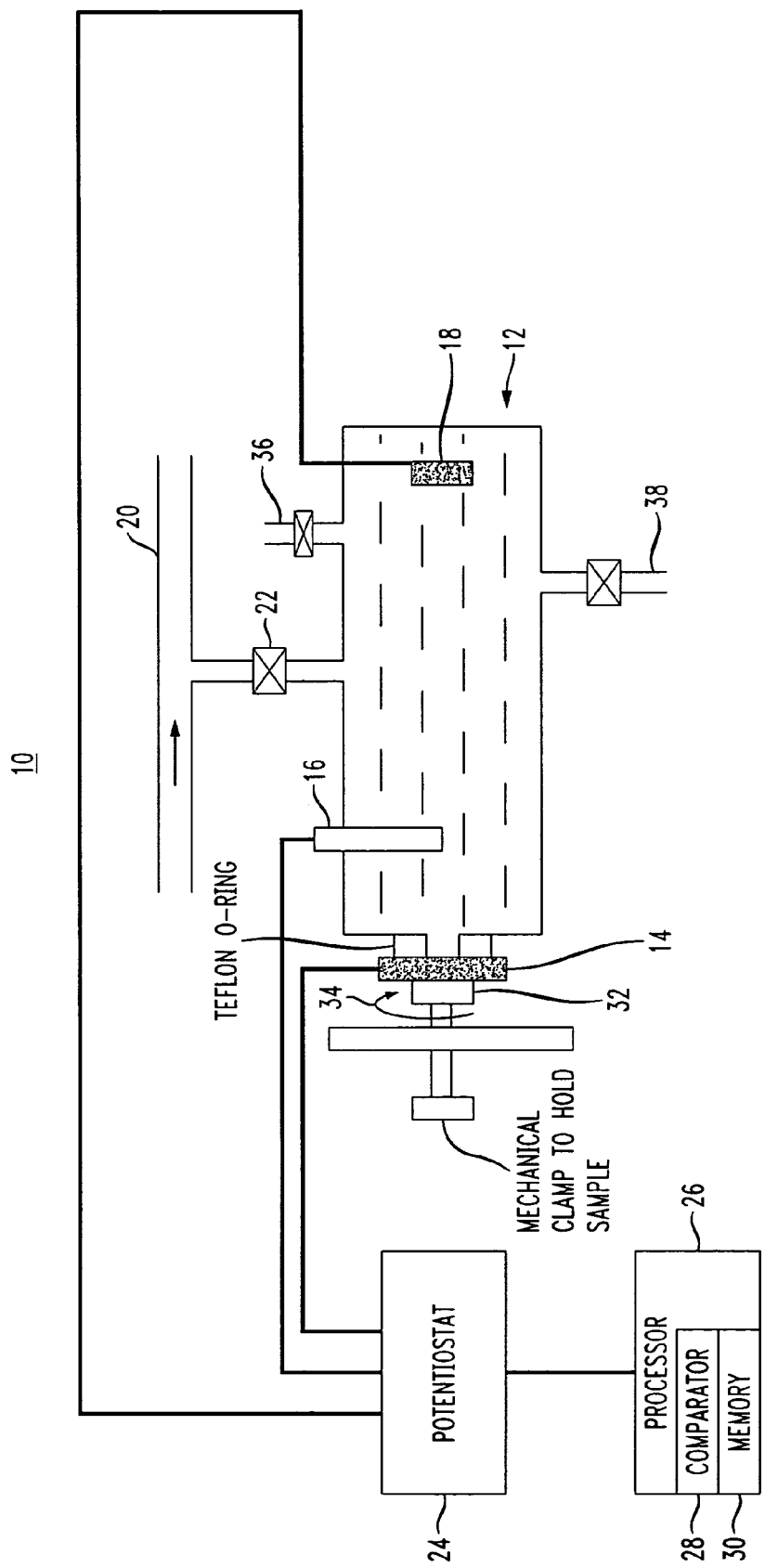
FIG. 4 illustrates an exemplary monitoring system embodying aspects of the present invention for determining hydrogen peroxide concentrations in a respective slurry, such as chemical mechanical polishing slurry for removing tungsten material.

FIG. 4 illustrates an exemplary monitoring system 10 embodying aspects of the present invention. In one form, monitoring system 10 includes an electrochemical cell 12 made up of a working electrode 14, a reference electrode 16 and a counter electrode 18. However, it will be recognized that the system could use only a working electrode and a counter electrode by suitable selection of the types of electrodes. The electrochemical cell is fluidly coupled to receive slurry including hydrogen peroxide from a CMP process line 20, through an inlet valve 22. As will be readily appreciated by those skilled in the art, the cell 12 may be placed at any suitable location in the CMP process line, including by way of example, a feed line of a CMP tool, a slurry storage tank associated with a CMP tool, a slurry outlet line of a CMP tool, etc. As suggested above, a potentiostat 24 is provided for maintaining the potential at the working electrode at a desired value and measure current flow between the working electrode and the counter electrode. As will be appreciated by those skilled in the art, the potentiostat includes a regulated power supply and feedback system that may use standard closed-loop control techniques for accurately controlling the potential applied to the working electrode, and is commercially available from Princeton Applied Research, Gamry Instruments, Inc., or other suppliers of electrochemical instrumentation. The power supply regulates the current to the electrode to maintain the regulated voltage. As used herein and consistent with terminology readily understood by those skilled in the art, the reference electrode represents the electrode against which the potential of the working electrode is measured. The reference electrode is typically a silver/silver chloride, or saturated calomel electrode, which are commercially available. The working electrode represents the electrode where the reaction of interest takes place and in one exemplary embodiment comprises tungsten. The counter electrode represents the electrode that provides a current path in the electrochemical cell and typically comprises graphite. Those skilled in the art will understand, however, that any inert conductor is usable, such as platinum, gold, rhodium or glassy carbon. The counter electrode itself may also serve as reference electrode if it is stable in and immune to the hydrogen peroxide slurry. This will alleviate the need for a separate reference electrode. Platinum, for example, could be used for this purpose. It is also recognized that materials other than tungsten could be used for the working electrode as long as an oxide layer is formed on such electrode at a rate proportional to $H_2O_2$ concentration.

As suggested above, the amount of passive current between the working electrode and the counter electrode over a selected time window is indicative of the concentration of hydrogen peroxide in the slurry. Potentiostat 24 may be connected to a processor 26 to process the amount of current that passes through the slurry over time. As will be appreciated by those skilled in the art, processor 26 may be integrated with potentiostat 24 or may be a computer or microprocessor separate from potentiostat 24. Regardless of the specific implementation, processor 26 may include a comparator 28 configured to relate or compare the value of current provided by the potentiostat 24 against a functional relationship for determining the hydrogen peroxide concentration in the slurry. The current value is provided by the commercially available potentiostat or voltage regulator which sets the current needed to maintain the regulated output voltage. The functional relationship may be stored in a memory device 30, e.g., a look-up table, and would reflect experimentally and/or analytically derived values, such as those respectively plotted in FIGS. 1–3 for illustrating exemplary relationships between passive current and peroxide concentration in a given slurry. It will be appreciated by those skilled in the art, that in lieu of using a look-up table, one could use a straightforward equation or mathematical relationship for computing the peroxide concentration in the slurry based on the current measured in the electrochemical cell. It will be further understood that any of the various arithmetic and logical operations performed in the processor may be conducted through respective software modules as may be executed by the microprocessor or computer and such operations need not be executed through hardware modules.

Benefits:

As will be now recognized by those skilled in the art, the techniques and monitoring system in accordance with aspects of the present invention are advantageously suitable for on-line monitoring applications. The hardware/software requirements are relatively simple and inexpensive: an electrochemical instrument for controlling the potential applied to the working electrode (e.g., potentiostat 24), and a processor configured to perform the operational interrelationships described above.

In one exemplary embodiment, for ensuring generally continuous monitoring, the tungsten sample or working electrode may be configured as a relatively thin roll of tungsten. A motorized roll holder assembly 32 that may expose fresh tungsten for each new measurement, as conceptually represented by arrow 34. For example, the motorized assembly may be purchased from Pine Instrument Co. It is believed that this would generally ensure uniform exposure of the working electrode relative to the slurry. The rotation may serve to keep slurry particles dispersed and may facilitate mass transport of species being oxidized or reduced during the measurement process. It will be understood, however, that rotation of the working electrode and slurry flow is not a requirement.

The techniques of the present invention conveniently avoid contamination of the CMP process line. The slurry is fed into the analysis cell using a gravity feed mechanism, for example. This eliminates the need for a generally costly (and potentially vulnerable to contamination) pump system to introduce or remove the slurry from the cell. As shown in FIG. 4, an outlet valve 38 may be provided to easily discharge the slurry from the cell. A deionized (DI) water inlet 36 may be used for introducing DI water for rinsing slurry residues from the cell, if so needed. As suggested above, the electrochemical cell would generally be placed to receive some of the CMP slurry flow so that the electrodes in the cell are constantly exposed to the slurry, which would enter the cell through inlet 22 and exit through outlet 38.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. An electrochemically-based method for determining hydrogen peroxide concentration in a slurry comprising:
   fluidly coupling an electrochemical cell to receive a chemical mechanical polishing slurry including hydrogen peroxide, the cell including at least a working electrode comprising tungsten, and a counter electrode;
   applying a desired potential to the working electrode;
   measuring current flow between the working electrode and the counter electrode; and
   determining the concentration of hydrogen peroxide in said slurry from the measured current.

2. The method of claim 1 wherein the measured current is coupled to a processor having a memory and further comprising storing in the memory a predefined relationship between current measurements and hydrogen peroxide concentration.

3. The method of claim 2 further comprising relating the current measurements between the working electrode and the counter electrode relative to the predefined relationship stored in memory to determine the concentration of hydrogen peroxide in the slurry.

4. The method of claim 1 further comprising configuring the working electrode as a relatively thin roll of tungsten.

5. The method of claim 4 further comprising rotating the working electrode to ensure generally uniform exposure of the working electrode relative to the slurry.

6. The method of claim 1 and including a reference electrode immersed in the slurry for providing a measurement of potential applied to the working electrode.

* * * * *